United States Patent [19]

Cavazza et al.

[11] Patent Number: 4,590,209
[45] Date of Patent: * May 20, 1986

[54] ALKOXY-ACYL CARNITINES AND PHARMACEUTICAL COMPOSITIONS CONTAINING SAME

[75] Inventors: Claudio Cavazza; Paolo De Witt; Maria O. Tinti; Emma Quaresima, all of Rome, Italy

[73] Assignee: Sigma-Tau Industrie Farmaceutiche Riunite S.p.A., Rome, Italy

[*] Notice: The portion of the term of this patent subsequent to Nov. 5, 2002 has been disclaimed.

[21] Appl. No.: 522,546

[22] Filed: Aug. 11, 1983

Related U.S. Application Data

[63] Continuation of Ser. No. 265,008, May 19, 1981, abandoned.

[30] Foreign Application Priority Data

May 30, 1980 [IT] Italy .................. 48854 A/80

[51] Int. Cl.$^4$ .................. C07C 101/30; A61K 31/22
[52] U.S. Cl. .................. 514/547; 560/187
[58] Field of Search .................. 560/170, 185, 187; 424/311; 514/547

[56] References Cited

U.S. PATENT DOCUMENTS

| | | | |
|---|---|---|---|
| 3,922,340 | 11/1975 | Miwa | 424/311 |
| 4,032,641 | 6/1977 | Chibata | 424/266 |
| 4,194,006 | 3/1980 | Cavazza | 424/311 |
| 4,237,167 | 12/1980 | Cavazza | 424/311 |

FOREIGN PATENT DOCUMENTS

| | | |
|---|---|---|
| 37-5174 | 6/1962 | Japan . |
| 241963 | 1/1963 | Japan . |
| 2021414 | 12/1979 | United Kingdom . |
| 2028826 | 3/1980 | United Kingdom . |

OTHER PUBLICATIONS

Wilson, "Textbook of Organic Medical and Pharmaceutical Chemistry," pp. 39–40 (1954).
Strack, Chem. Abst. 64: 19398 (1966).
Mino, Chem. Abst. 77: 151503 (1972).

Primary Examiner—Michael L. Shippen
Attorney, Agent, or Firm—Ladas & Parry

[57] ABSTRACT

A novel class of alkoxy-acyl carnitines, wherein the alkoxy-acyl radical has from 4 to 6 carbon atoms (tipically: methoxypropionyl, ethoxypropionyl and propoxyacetyl) is prepared by reacting a solution of a carnitine salt in an organic solvent with an alkoxy-acyl halogenide, thus obtaining the corresponding salt of alkoxy-acyl carnitine. By eluting an aqueous solution of this salt through a column of an ion exchange resin activated in $Cl^-$ or $Br^-$ form, the chloride or bromide of alkoxyacyl carnitine is obtained. The alkoxy-acyl carnitines are therapeutically effective in the treatment of cardiac disorders, hyperlipidaemias and hyperlipoproteinaemias.

5 Claims, No Drawings

ALKOXY-ACYL CARNITINES AND PHARMACEUTICAL COMPOSITIONS CONTAINING SAME

This is a continuation of co-pending application Ser. No. 265,008 filed May 19, 1981, abandoned.

The present invention relates to a novel class of alkoxy-acyl carnitines, the process for their preparation, the pharmaceutical compositions comprising such compounds and their use in therapy.

More particularly, the present invention relates to alkoxy-acyl carnitines having general formula (I):

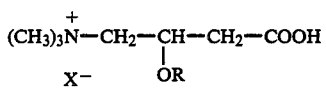

wherein:
 $X^-$ is an halogen anion selected between chlorine and bromine, preferably chlorine; and
 R is an alkoxy-acyl radical having from 4 to 6 carbon atoms, this radical being preferably selected in the class consisting of 2- and 3-methoxypropionyl, 2- and 3-ethoxypropionyl, propoxyacetyl and 4-methoxybutyryl.

It should be understood that the foregoing general formula (I) encompasses the compounds of the present invention both in their optically active forms and their racemic form.

It has been found that the compounds of the present invention possess valuable pharmacological properties and can, therefore, be utilized in the therapeutical field.

More particularly: The compounds of formula (I) showed to be endowed with a prolonged and effective inotropic action and devoid of any effects depressing the myocardial excitability.

Moreover, the compounds of formula (I) have shown to be endowed with an antifibrillation effect.

The direct antiarrhythmic activity of the quinidine type is complemented by the adrenaline-antagonizing activity.

The compounds of formula (I) have been shown to restore the α- and β-lipoprotein ratio to normal.

Therefore, the compounds of this invention can be therapeutically utilized:
(a) in cases of myocardial hypocontractility, such as in cardiogenic shock provoked by primary absence of contractile force;
(b) for the treatment of functional arrhythmias and arrhythmias secondary to myocardial-sclerotic processes; and
(c) for the treatment of hyperlipidaemias and hyperlipoproteinaemias.

The process for preparing the alkoxy-acyl carnitines halogenides of general formula (I) comprises the steps of:
(a) dissolving a salt of carnitine soluble in organic solvents in an organic solvent, preferably selected between trifluoroacetic acid and acetonitrile;
(b) adding to the solution thus obtained an alkoxy-acyl halogenide of formula RX wherein R has the previously specified meaning and X is an halogen selected between chlorine and bromine, and keeping the resulting reaction mixture at a temperature comprised between about room temperature and 40° C. for about 2–16 days, thus obtaining the corresponding salt of alkoxy-acyl carnitine; and, if that be the case
(c) converting the salt of alkoxy-acyl carnitine of step (b) into the halogenide of alkoxy-acyl carnitine of formula (I), treating an aqueous solution of said salt with an ion exchange resin activated in the $X^-$ form.

Preferably, the salt of carnitine of step (a) is selected from the class consisting of carnitine perchlorate (in this case the organic solvent being acetonitrile) and carnitine hydrochloride (in this case the organic solvent being trifluoroacetic acid).

The following non-limiting examples aim at illustrating the preparation of some alkoxy-acyl carnitines in accordance with the present invention.

EXAMPLE 1

Preparation of 3-ethoxypropionyl carnitine hydrochloride (1) Preparation of the 3-ethoxypropionyl chloride 7.7 cc (0.09 moles) of oxalyl chloride were added to 3.3 cc (0.03 moles) of 3-ethoxypropionic acid. The reaction mixture was allowed to stand for about 4 hours at room temperature under magnetic stirring. At this time the reaction showed to be complete. The excess of oxalyl chloride was evaporated under vacuum and a number of washings with anhydrous ethyl ether were carried out.

(2) Preparation of 3-ethoxypropionyl carnitine perchlorate 3.9 g (0.015 moles) of carnitine perchlorate were dissolved in 50 cc of anhydrous $CH_3CN$. To this solution 3-ethoxypropionyl chloride was added dropwise with a dropping funnel while cooling to about 0° C. with an ice bath. The reaction mixture was allowed to stand for 48 hours at room temperature (TLC chloroform-methanol-water-$NH_4OH$ 55:35:5:5). During this period of time a stream of nitrogen was blown into the reaction mixture at intervals of about 5 minutes, in order to remove the hydrochloric acid formed during the reaction. The reaction mixture was slowly poured into 300 cc of ethyl ether. A precipitate was thus obtained which was taken up with anhydrous acetone and the resulting solution was allowed to stand for some hours. The solution was filtered and ethyl ether was added thereto and a precipitate formed. The precipitate dried under vacuum presented the appearence of a transparent and viscous oil which consisted of 3-ethoxypropionyl carnitine perchlorate.

(3) Convertion into 3-ethoxypropionyl carnitine hydrochloride

An aqueous solution of 3-ethoxypropionyl carnitine perchlorate was passed through IRA 402 resin in $Cl^-$ form, thus obtaining the title compound. 3-ethoxypropionyl carnitine hydrochloride is a microcrystalline, white solid. Yield 92%. Melting point: 169°–170° C.

NMR $D_2O$ δ 5.40–5.86 (1H,m,

3.33–3.86 (6H,m,$CH_2OCH_2$—;

3.20 (9H,s, 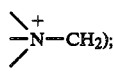

2.60–2.90 (4H,m,—CH₂CH₂CO—, —CH₂COOH); 1.13 (3H,t,OCH₂CH₃)

| TLC | CHCl₃, | MetOH, | H₂O, | NH₄OH |
|---|---|---|---|---|
| — | 55 | 35 | 5 | 5 |

EXAMPLE 2

Preparation of 4-methoxybutyryl carnitine (1) Preparation of 4-methoxybutyric acid 70.5 g (0.82 moles) of γ-butyro lactone were added to a solution of 18.9 g (0.82 moles) of metal sodium in 210 ml of methanol. The mixture was refluxed for 36 hours and then concentrated under vacuum. The residue was dissolved in water and acidified with concentrated hydrochloric acid. The resulting aqueous solution was three times extracted with ethyl ether. The ethyl ether solution was concentrated under vacuum and the residue was distilled. The fraction distilling at 112°–115° C./12 mmHg consists of pure 4-methoxy butyric acid, as confirmed by NMR analysis.

(2) Preparation of 4-methoxybutyryl chloride 27 g (0.23 moles) of 4-methoxybutyric acid were suspended in 150 cc of petroleum ether. To the resulting mixture a solution of 25 cc of thionyl chloride in 50 cc of petroleum ether was slowly added. The resulting mixture was kept under stirring overnight at room temperature. The raw product thus obtained was used as such in the subsequent reaction.

(3) Preparation of 4-methoxybutyryl carnitine 4.5 g (0.02 moles) of carnitine hydrochloride were dissolved in 6 ml of trifluoroacetic acid. To this solution 4-methoxybutyryl chloride was added. The resulting mixture was kept under stirring at room temperature for 16 days. Subsequently tert-butyl methyl ether was added to the mixture. An oil precipitated which was treated with anhydrous acetonitrile in order to remove the undesired carnitine. To the acetonitrile solution tert-butyl methyl ether was added and 4-methoxybutyryl carnitine precipitated. Yield 50%.

NMR D₂Oδ5.6 (1H,s,

3.8 (2H,d,—CH₂OCH₃); 3.5 (2H,d, 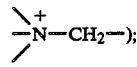

3.3 (3H,s,—OCH₃); 3.2 (9H,s,

CH₃  
CH₃—N);  
CH₃

2.8 (2H,d,—CH₂COOH); 2.5 (2H,t,—OCOCH₂—); 1.8 (2H,m,—CH₂CH₂OCH₃)

PHARMACOLOGICAL ACTIVITIES

The pharmacological properties of the compounds of the present invention were investigated with the following techniques:

(a) Acute toxicity (LD50)

Acute toxicity was investigated by using the method disclosed by Weil C. S. in "Tables for convenient calculation of median-effective dose (LD50 or ED50) and instructions in their use", Biometrics, 249–253, 1952.

The tolerance of the compounds under examination was investigated in mice after administration by the intraperitoneal or oral route. The obtained results show that the compounds exhibit excellent tolerance. (see the Table).

(b) Inotropic effect

Rabbit hearts isolated by the Langendorff method were perfused with oxygenized Ringer solution at 38.2° C. The isometric contractions, electrogardiogram and coronary flow were recorded using a "Battaglia-Rangoni" polygraph. By removing the oxygen from the perfusion fluid, metabolic damage was induced in the cardiac muscle, up to an 80% reduction in the cardiac contractile force.

Under these conditions of prolonged anoxia the aerobic glycolysis of the myocardium is slowed down, accompanied by the storage of acid catabolites due to both the accumulation of pyruvic acid and its conversion to lactic acid which cannot be utilized because of the depression of pyridine enzymes, such as LDH (lactodehydogenase). This has repercussions on the anaerobic glycolysis affecting an ever increasing number of enzymes, accompanied by a progressive and increasingly critical exhaustion of the myocardium. Thus a whole series of cardiac muscle fatigue levels occurs which can be observed by the behavior of the examined parameters, namely the contractile force, coronary flow, heart rate and cardiac rhythm. As soon as the contractile force was reduced by 80%, the perfusion fluid was once again oxygenized either without adding other compounds (controls) or with the addition of the compounds under examination.

The contractile force of the heart was examined, which shows a positive inotropic effect after 10 minutes from the interruption of the anoxic period (myocardial restoration). The results, evaluated by means of Student's "t" test, show that the compounds under examination induce a positive inotropic effect statistically significant against the controls.

In the Table there are shown the percentage value of increase against the controls.

(c) Antiarrhythmic effect

In order to evaluate the antiarrhythmic activity of the carnitine derivatives of this invention studied with in vivo tests in addition to and in comparison with the currently employed in vitro tests, the method disclosed by Nwangwu et al. (Arch. Inc. Pharmacodyn., 1977, 229, 219) was used.

According to this method an aconitine solution is injected into the caudal vein of mice and the onset time of arrhythmia and tachycardia after 2 to 60 minutes from administration of the compounds under examination is recorded.

The antiarrhythmic activity calculated from the increase in the latency time of the onset of the arrhythmias of the treated animals in comparison with the controls, is illustrated in the Table.

(d) Adrenaline-antagonizing effect.

Groups of ten male Albino Swiss mice, weighing 12-22 g, were intraperitoneally administered either with the compounds of the present invention or with saline (control) and, after 30 minutes, with adrenaline (treated) at a dose capable of bringing about death to 100% of the control animals due to ventricular fibrillation and cardiac lesions ensuing from increase in frequency, pressure and oxygen uptake from the myocardium.

Mortality was checked for 36 hours and the effect of the compounds expressed as percentage of surviving animals, is shown in the Table.

which will be apparent to the experts of pharmaceutical techniques.

The dose to be administered will be determined by the attending physician taking the age, weight and general conditions of the patient into account, utilizing sound professional judgment. Although effective results can be observed even at doses as low as from about 5 to 8 mg/kg of body weight daily, a daily dose of from about 10 to about 50 mg/kg of body weight is preferred. Should it be deemed necessary, larger doses can be administered, in view of the low toxicity of the compounds of this invention.

Non-limiting example of dosages are as follows:
fials: 5–500 mg
capsules: 15–50 mg
tablets: 15–500 mg
oral solutions: 15–50 mg

What is claimed is:

1. An alkoxy-carboxyl carnitine halogenide having the general formula I $$(CH_3)_3\overset{+}{N}-CH_2-\underset{\underset{OR}{|}}{CH}-CH_2-COOH \quad X^- \quad (I)$$

wherein: $x^-$ is a chlorine or bromine; and R is an alkoxy substituted saturated aliphatic monocarboxylic acid radical having 4 to 6 carbon atoms, excluding ethoxyacetyl and excluding alicyclic compounds.

2. A compound according to claim 1, wherein said radical R is selected from the class consisting of 2- and 3-methoxy-propionyl, 2- and 3- ethoxypropionyl, pro-

TABLE

Pharmacological activity of some alkoxy-acyl carnitines.
LD$_{50}$ by the intraperitoneal route in mice, antifibrillatory activity in mice, adrenaline-antagonizing activity in mice, inotropic activity on rabbit isolated heart.

| 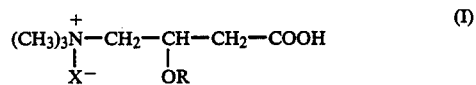 | LD$_{50}$ mg kg$^{-1}$ i.p. | Antifibrillatory activity (dose mg kg$^{-1}$ i.v.) % reduction | Antiadrenaline activity (dose mg kg$^{-1}$ i.p.) % mortality reduction | Inotropic effect (dose $10^{-5}$ gl$^{-1}$) % of controls |
|---|---|---|---|---|
| R = 3-ethoxypropionyl | 1300 | 80 (300) | 75 (450) | +95 |
| R = 4-methoxybutyryl | 1850 | 85 (25) | 78 (50) | +85 |

The compounds of the present invention are administered either orally or parenterally, in any one of the usual pharmaceutical forms which are prepared by conventional procedures, well known to the experts in the pharmaceutical field. These forms comprise solid and liquid oral unit dosage forms, such as tablets, capsules, solutions, syrups, and the like and injectable forms such as sterile solutions for ampoules and vials.

For preparing such pharmaceutical forms the usual solvents, diluents and excipients are used. Optionally, preservative, sweetening and flavoring agents can also be present. Non limiting examples of such substances are sodium carboxymethyl cellulose, polysorbate, mannitol, sorbitol, starch, avicel, talc and other substances poxyacetyl and 4-methoxybutyryl.

3. A compound according to claim 1 or 2, in their optically active forms.

4. A compound according to claim 1 or 2, in their racemic form.

5. A pharmaceutical composition for treating cardiac disorders, hyperlipoproteinaemia or hyperlipidemia which comprises a halogenide of formula (I) as defined in claim 1 in an amount effective in the treatment of cardiac disorders, hyperlipoproteinaemia or hyperlipidemia, and a pharmacologically acceptable excipient.

* * * * *